US012642944B2

(12) United States Patent
Nandakumar et al.

(10) Patent No.: US 12,642,944 B2
(45) Date of Patent: Jun. 2, 2026

(54) CATHETER SYSTEM HAVING A PUSH BUTTON SAFETY DEVICE

(71) Applicant: Becton, Dickinson and Company, Franklin Lakes, NJ (US)

(72) Inventors: Sridhaar Nandakumar, Chennai (IN); Prasad Govindaraj, Coimbatore (IN); Nandha Krishnan, Coimbatore (IN); Mohamed Shafiq, Bangalore (IN); Sankaranarayan Thirumoorthy, Madurai (IN); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 696 days.

(21) Appl. No.: 18/094,749

(22) Filed: Jan. 9, 2023

(65) Prior Publication Data

US 2023/0233810 A1     Jul. 27, 2023

Related U.S. Application Data

(60) Provisional application No. 63/302,429, filed on Jan. 24, 2022.

(51) Int. Cl.
*A61M 25/06* (2006.01)
*A61M 25/00* (2006.01)

(52) U.S. Cl.
CPC .... *A61M 25/0631* (2013.01); *A61M 25/0097* (2013.01); *A61M 25/0606* (2013.01)

(58) Field of Classification Search
CPC ...................... A61M 25/0631; A61M 25/0606
See application file for complete search history.

(56) References Cited

U.S. PATENT DOCUMENTS

| | | | |
|---|---|---|---|
| 5,501,675 A | 3/1996 | Erskine | |
| 2002/0151847 A1 | 10/2002 | Takagi et al. | |
| 2016/0067453 A1* | 3/2016 | Braithwaite ...... | A61M 25/0631 |
| | | | 604/164.08 |
| 2021/0260338 A1 | 8/2021 | Scherich | |

FOREIGN PATENT DOCUMENTS

WO          02066093 A2     8/2002

* cited by examiner

*Primary Examiner* — Courtney B Fredrickson
(74) *Attorney, Agent, or Firm* — Kirton McConkie; Whitney Blair; Kevin Stinger

(57) ABSTRACT

A catheter system may include a catheter assembly and a needle assembly. The needle assembly may include a cover disposed over a push button. An inner surface of the cover may include a projection, and the cover may be configured to slide proximally. In response to the cover sliding proximally, the projection may be configured to contact the push button, and the push button may be configured to depress. The push button may include a living hinge. The housing may include a flange contacting a proximal end of the push button to prevent the proximal end of the button from being depressed. In response to bending of the living hinge, the push button may be configured to move distal to the flange and depress. In response to depression of the push button, the needle hub may move proximally within the barrel to retract the introducer needle.

15 Claims, 19 Drawing Sheets

CATHETER SYSTEM HAVING A PUSH BUTTON SAFETY DEVICE

RELATED APPLICATIONS

This application claims the benefit of U.S. Provisional Patent Application No. 63/302,429, filed Jan. 24, 2022, and entitled CATHETER SYSTEM HAVING A PUSH BUTTON SAFETY DEVICE, which is incorporated herein in its entirety.

BACKGROUND

A common type of catheter assembly includes a peripheral intravenous catheter ("PIVC") that is over-the-needle. As its name implies, the PIVC that is over-the-needle may be mounted over an introducer needle having a sharp distal tip. The catheter assembly may include a catheter adapter, the PIVC extending distally from the catheter adapter, and the introducer needle extending through the PIVC. The PIVC and the introducer needle may be assembled such that the distal tip of the introducer needle extends beyond the distal tip of the PIVC with the bevel of the needle facing up away from skin of the patient immediately prior to insertion into the skin. The PIVC and the introducer needle are generally inserted at a shallow angle through the skin into vasculature of the patient.

In order to verify proper placement of the introducer needle and/or the PIVC in the blood vessel, a clinician may confirm that there is flashback of blood in a flashback chamber of the catheter assembly. Once placement of the introducer needle has been confirmed, the clinician may remove the introducer needle, leaving the PIVC in place for future blood withdrawal or fluid infusion.

In some instances, the catheter assembly, such as the BD INSYTE™ AUTOGUARD™ Shielded IV Catheter, may include a push button configured to retract the introducer needle after the PIVC is in place within the vein. The push button may be accidentally or inadvertently activated before venipuncture completion, such as, for example, during assembly, packaging, shipping, or removal from packaging.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access devices and related methods. More particularly, the present disclosure relates to a catheter system that includes a push button safety device, as well as related devices and methods. In some embodiments, the push button safety device may prevent accidental or inadvertent retraction of an introducer needle before venipuncture is complete.

In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter assembly may include a catheter extending from the distal end of the catheter adapter. In some embodiments, the catheter may include a peripheral intravenous catheter, a peripherally-inserted central catheter, or a midline catheter.

In some embodiments, the catheter system may include a needle assembly, which may include a housing. In some embodiments, the housing may include a barrel. In some embodiments, the needle assembly may include the introducer needle, which may include a sharp distal tip. In some embodiments, the needle assembly may include a needle hub coupled the introducer needle and movably disposed within the barrel. In some embodiments, the needle assembly may include a spring disposed within the housing. In some embodiments, the needle assembly may include a push button.

In some embodiments, the needle assembly may include a cover disposed over the push button. In some embodiments, the push button safety device may include the cover. In some embodiments, an inner surface of the cover may include a projection. In some embodiments, the cover may be configured to slide proximally. In some embodiments, in response to the cover sliding proximally, the projection may be configured to contact the push button to depress the push button. In some embodiments, in response to depression of the push button, the spring may be configured to expand proximally and move the needle hub proximally within the barrel to retract the introducer needle proximally. In some embodiments, the push button may include a projection for engagement with the catheter adapter to prevent depression of the push button when the catheter adapter is proximate the catheter adapter.

In some embodiments, the cover may be U-shaped and configured to fit over a top of the needle assembly. In some embodiments, the inner surface of the cover may include multiple rails on opposing sides of the inner surface of the cover. In some embodiments, an outer surface of the housing may include multiple elongated guides on opposing sides of the housing and contacting the rails. In some embodiments, the rails may be configured to slide along the elongated guides when the cover slides proximally. In some embodiments, each of the elongated guides may include a groove. In some embodiments, each of the elongated guides may include a flange.

In some embodiments, at least one of the elongated guides may include a housing snap projection. In some embodiments, the inner surface of the cover may include a cover snap projection. In some embodiments, the housing snap projection may be proximal to the cover snap projection. In some embodiments, the cover snap projection may be configured to snap past the housing snap projection in response to the cover sliding proximally.

In some embodiments, the inner surface of the cover may include another rail. In some embodiments, the cover snap projection may extend from the other rail. In some embodiments, the needle assembly may include multiple shafts disposed on opposing sides of the housing. In some embodiments, the cover may be configured to slide along the shafts.

In some embodiments, the cover may include multiple openings on opposing sides of the cover. In some embodiments, the shafts may extend through the openings. In some embodiments, each of the shafts may include at least one step. In some embodiments, the at least one step may be configured to contact the cover to provide resistance to proximal movement of the cover.

In some embodiments, the cover may include multiple rings forming the openings. In some embodiments, multiple arms may extend proximally from the rings. In some embodiments, a top surface of the cover may be angled upwardly in a proximal direction. In some embodiments, the top surface may include multiple ribs extending generally perpendicular to a longitudinal axis of the catheter system.

In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter assembly may include a catheter extending from the distal end of the catheter adapter. In some embodiments, the catheter may include a peripheral intravenous catheter, a peripherally-inserted central catheter, or a midline catheter.

In some embodiments, the catheter system may include a needle assembly, which may include a housing. In some embodiments, the housing may include a barrel. In some embodiments, the needle assembly may include an introducer needle, which may include a sharp distal tip. In some embodiments, the needle assembly may include a needle hub coupled the introducer needle and movably disposed within the barrel. In some embodiments, the needle assembly may include a spring disposed within the housing. In some embodiments, the needle assembly may include a push button.

In some embodiments, the push button safety device may include a push button that is configured to depress after distal movement of the push button. In further detail, in some embodiments, the push button may include a living hinge. In some embodiments, the housing may include a flange contacting a proximal end of the push button to prevent the proximal end of the push button from being depressed. In some embodiments, in response to bending of the living hinge, the proximal end of the push button may be configured to move distal to the flange and the push button may be configured to depress. In some embodiments, in response to depression of the push button, the spring may be configured to expand proximally and move the needle hub proximally within the barrel to retract the introducer needle proximally.

In some embodiments, the push button may include a projection for engagement with the catheter adapter to prevent movement of the push button when the catheter adapter is adjacent to a distal end of the barrel. In some embodiments, the proximal end of the button proximal to the living hinge may include multiple grip features. In some embodiments, the flange may be proximate a cavity in the housing. In some embodiments, the push button may be configured to depress into the cavity in response to bending of the living hinge and movement of the proximal end of the push button is distal to the flange. In some embodiments, a distal end of the push button may be proximate the housing when the flange contacts the proximal end of the push button.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
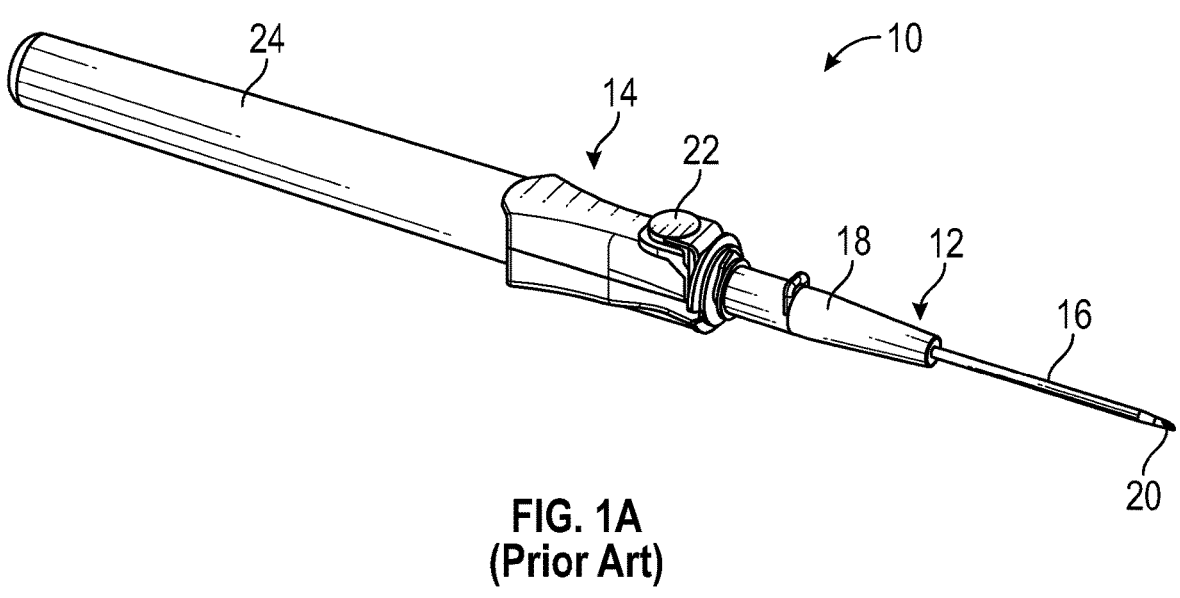
FIG. 1A is an upper perspective view of a prior art catheter system, according to some embodiments.

Referring now to FIG. 1A, a prior art catheter system 10 is illustrated. The prior art catheter system 10 includes a catheter assembly 12 coupled to a needle assembly 14. The catheter assembly 12 includes a catheter 16 extending distally from a distal end of a catheter adapter 18. The needle assembly 14 includes an introducer needle 20 extending through the catheter 16 to facilitate insertion of the catheter 16 through a vein of a patient.

The needle assembly 14 includes a push button 22 configured to retract the introducer needle 20 into a barrel 24 of the needle assembly 14 when the push button 22 is pushed or depressed. Some examples of catheter systems that may include the push button 22 are the BD INSYTE™ AUTO-GUARD™ Shielded IV Catheter, the BD INSYTE™ AUTOGUARD™ BC Shielded IV Catheter, and the Accu-Cath ACE™ Intravascular Catheter, all available from Becton Dickinson & Company of Franklin Lakes, New Jersey. Another example of a catheter system that may include the push button 22 is the SUPERCATH™ 5 Safety IV Catheter, available from ICU Medical of San Clemente, California. The push button 22 and retraction of the introducer needle 20 help reduce needle stick injuries. Unfortunately, in some cases, the push button 22 may be accidentally or inadvertently activated by a user before venipuncture completion, such as, for example, due to mishandling or during assembly, packaging, shipping, or removal from packaging.

Referring now to FIGS. 1B-1I, in some embodiments, a catheter system 30 may reduce or eliminate accidental activation of a push button by restricting access to a push button. In some embodiments, the catheter system 30 may include a catheter assembly 32, which may include a catheter adapter 34. In some embodiments, the catheter adapter 34 may include a distal end 36, a proximal end 38, and a catheter adapter lumen 40 extending through the distal end 36 of the catheter adapter 34 and the proximal end 38 of the catheter adapter 34. In some embodiments, the catheter assembly 32 may include a catheter 42 extending from the distal end 36 of the catheter adapter 34. In some embodiments, the catheter 42 may include a peripheral intravenous catheter, a peripherally-inserted central catheter, or a midline catheter.

In some embodiments, the catheter system 30 may include a needle assembly 44, which may include a housing 46. In some embodiments, the housing 46 may include a barrel 48. In some embodiments, the needle assembly 44 may include the introducer needle 50, which may include a sharp distal tip 52 and a proximal end 54. In some embodiments, the needle assembly 44 may include a needle hub 56 coupled the introducer needle 50 and movably disposed within the barrel 48, which may shield the user from the introducer needle 50 and/or blood after retraction of the introducer needle 50 into the barrel 48. In some embodiments, the needle assembly 44 may include a spring 58 disposed within the housing 46. In some embodiments, the needle assembly 44 may include a push button 60.

In some embodiments, the push button 60 may operate similar to the activation latch described in U.S. Pat. No. 5,501,675, filed Dec. 27, 1994, entitled "SAFETY CATHETER ASSEMBLY HAVING SAFETY STOP PUSH BUTTON", which is hereby incorporated by reference in its entirety. In some embodiments, the push button 60 may operate in another manner to shield a particular introducer needle. In some embodiments, the spring 58 may be located about introducer needle 50, and the spring 58 may extend between the needle hub 56 and a distal end of barrel 48. In some embodiments, the push button 60 may extend into the barrel 48 via a cavity or slot formed in the barrel 48 adjacent to the distal end of the barrel 48. In some embodiments, the push button 60 may include an opening 64 configured to allow the introducer needle 50 and the needle hub 56 to extend through the push button 60. In some embodiments, the opening 64 may be keyhole shaped. In some embodiments, the push button 60 may include a projection 66 that may extend toward the distal end of catheter 42 and the catheter assembly 32.

In some embodiments, when push button 60 is "up" in a non-activated position, a smaller portion of the opening 64 may be in communication with a lumen 68 of the barrel 48. In some embodiments, in this position, the smaller portion of the opening 64 may engage the needle hub 56 and hold the needle hub 56 adjacent to the distal end of barrel 48 against the force of the spring 58. In some embodiments, the needle hub 56 may include a distal flare so that a medial portion of the needle hub 56 has a smaller diameter than the distal flare. In some embodiments, the needle hub 56 may include an hourglass shape. In some embodiments, the distal flare and/or the hourglass shape may facilitate engagement between the smaller portion of the opening 64 and the needle hub 56. In some embodiments, when the push button 60 is in the non-activated position, the projection 66 may be located inside the catheter adapter 34. Thus, in some embodiments, when the catheter 42 is still located on the introducer needle 50 with the catheter adapter 34 adjacent to the distal end of the housing 46, the projection 66 may prevent the push button 60 from being depressed or moved "down" into the activated position.

In some embodiments, the projection 66 may include a length of between about 0.5 mm and about 2.5 mm. In some embodiments, the length of the projection 66 should be long enough so the projection 66 engages the catheter adapter 34 when the catheter adapter 34 is adjacent to the distal end of the housing 46. However, in some embodiments, the projection 66 should not be so long that it interferes with the use of the catheter 42 and the introducer needle 50.

In some embodiments, when the catheter 42 is moved off the introducer needle 50 so the catheter adapter 34 is not adjacent to the distal end of housing 46, the push button 60 can be moved "down," i.e., activated, because the catheter adapter 34 no longer interferes with the movement of the projection 66. In some embodiments, in this position, a larger portion of the opening 64 may no longer engage the needle hub 56. In some embodiments, the larger portion of the opening 64 should be larger than the maximum diameter of the needle hub 56. In some embodiments, the spring 58 can thus force the needle hub 56 to a proximal end of the barrel 48 and withdraw the sharp distal tip 52 of the introducer needle 50 into the barrel 48.

In some embodiments, the projection 66 on the push button 60 can also be angled. This configuration allows the user to activate the push button 60 by pressing down firmly on the push button 60. In some embodiments, this downward force will transmit some axial force to catheter adapter 34 because of a wedge shape of the projection 66. In some embodiments, the catheter adapter 34 will then be advanced in the distal direction clearing the way for depression of the push button 60. In some embodiments, the wedge shape should be at an angle of between about 15 degrees and about 25 degrees to a longitudinal axis of the catheter adapter 34.

In some embodiments, the needle assembly 44 may include a cover 70 disposed over the push button 60 and configured to slide with respect to the housing 46. In some embodiments, the cover 70 may be disposed over any suitable push button that is configured to retract an introducer needle proximally. In some embodiments, the cover 70 may be configured to slide between a first position in which the cover 70 is on top of the push button 60 and a second position in which the cover 70 is offset from the push button 60, allowing access to the push button 60 by the user for depression of the push button 60. In some embodiments, the first position may be distal to the second position, which may facilitate movement of the cover 70 proximally with a single digit of the user, such as an index finger. In some embodiments, the cover 70 may be configured to slide by applying a linear force in a longitudinal direction or along a longitudinal axis of the catheter system 30. In some embodiments, because the linear force is configured to slide the cover 70 as opposed to a normal force, this may reduce a risk of accidental sliding of the cover 70.

In some embodiments, an inner surface 74 of the cover 70 may include a projection 72. In some embodiments, the cover 70 may be configured to slide proximally. In some embodiments, in response to the cover 70 sliding proximally, the projection 66 may be configured to contact the push button 60 to depress or activate the push button 60. In some embodiments, the projection 66 may be configured to contact the push button 60 to depress the push button when the catheter adapter 34 is spaced apart from the housing 46 (such that the projection 66 allows depression of the push button 60). In some embodiments, the push button 60 may not include the projection, and the projection 66 may be configured to contact the push button 60 to depress the push button when the catheter adapter 34 is spaced apart from the housing 46 or proximate the housing 46.

In some embodiments, the push button 60 may be depressed when the projection 72 contacts the push button 60 and/or the catheter adapter 34 is spaced apart from the housing 46 (such that the projection 66 allows depression of the push button 60). In some embodiments, in response to depression of the push button 60, the spring 58 may be configured to expand proximally and move the needle hub 56 proximally within the barrel 48 to retract the introducer needle 50 proximally. In some embodiments, the push button 60 may include the projection 66 for engagement with the catheter adapter 34 to prevent depression of the push button 60 when the catheter adapter 34 is proximate the housing 46, such as, e.g., contacting or fully seated with the housing 46.

In some embodiments, the cover 70 may be U-shaped and configured to fit over a top of the needle assembly 44. In some embodiments, the inner surface 74 of the cover 70 may include multiple rails 76 on opposing sides of the inner surface 74 of the cover 70. In some embodiments, an outer surface 78 of the housing 46 may include multiple elongated guides 80 on opposing sides of the housing 46 and contacting the rails 76. In some embodiments, the rails 76 may be configured to slide along the elongated guides 80 when the cover 70 slides proximally.

Figure 1B:
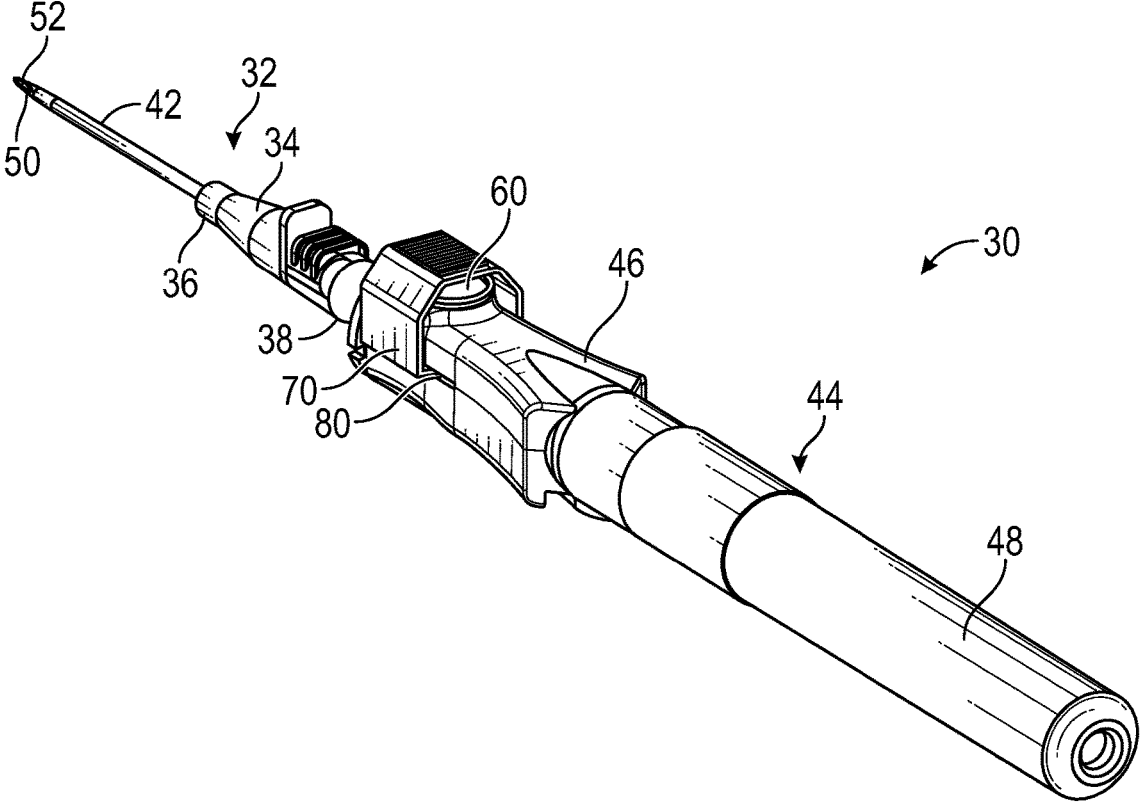
FIG. 1B is an upper perspective view of an example catheter system, illustrating an example cover, according to some embodiments.
Figure 1C:
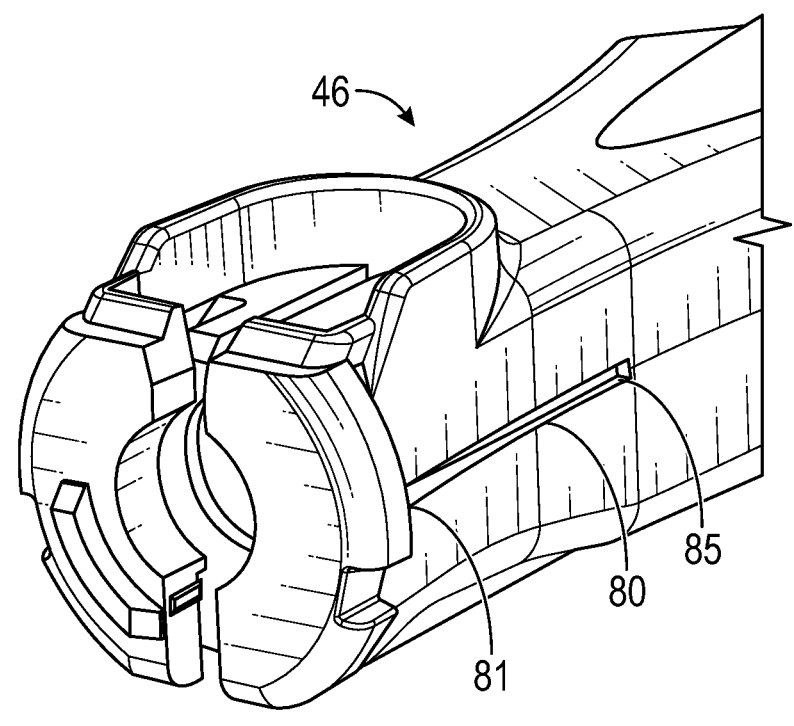
FIG. 1C is an upper perspective view of a distal end of an example housing, according to some embodiments.
Figure 1D:
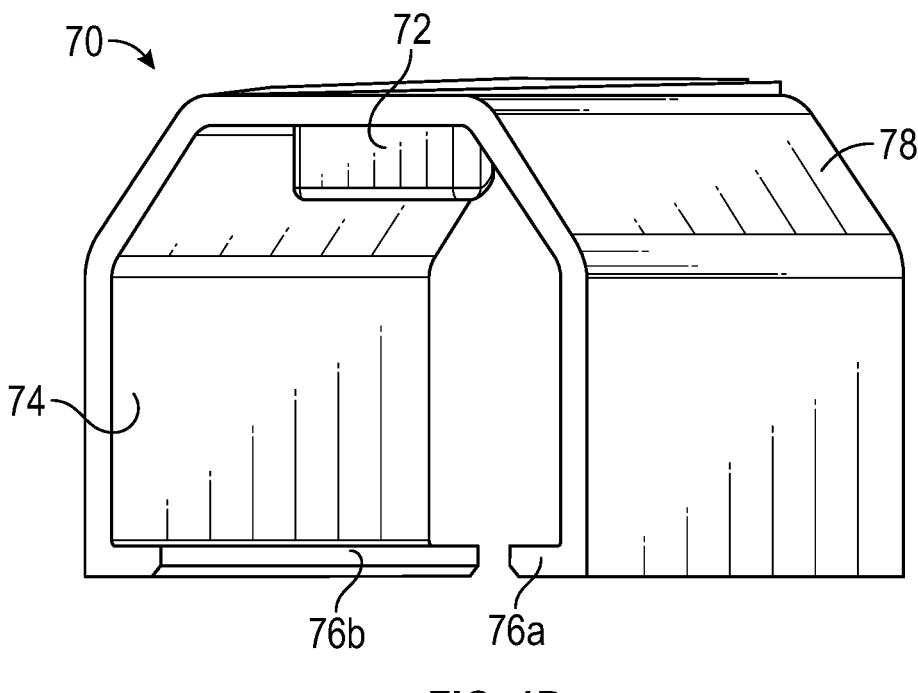
FIG. 1D is a lower perspective view of the cover of FIG. 1B, according to some embodiments.
Figure 1E:
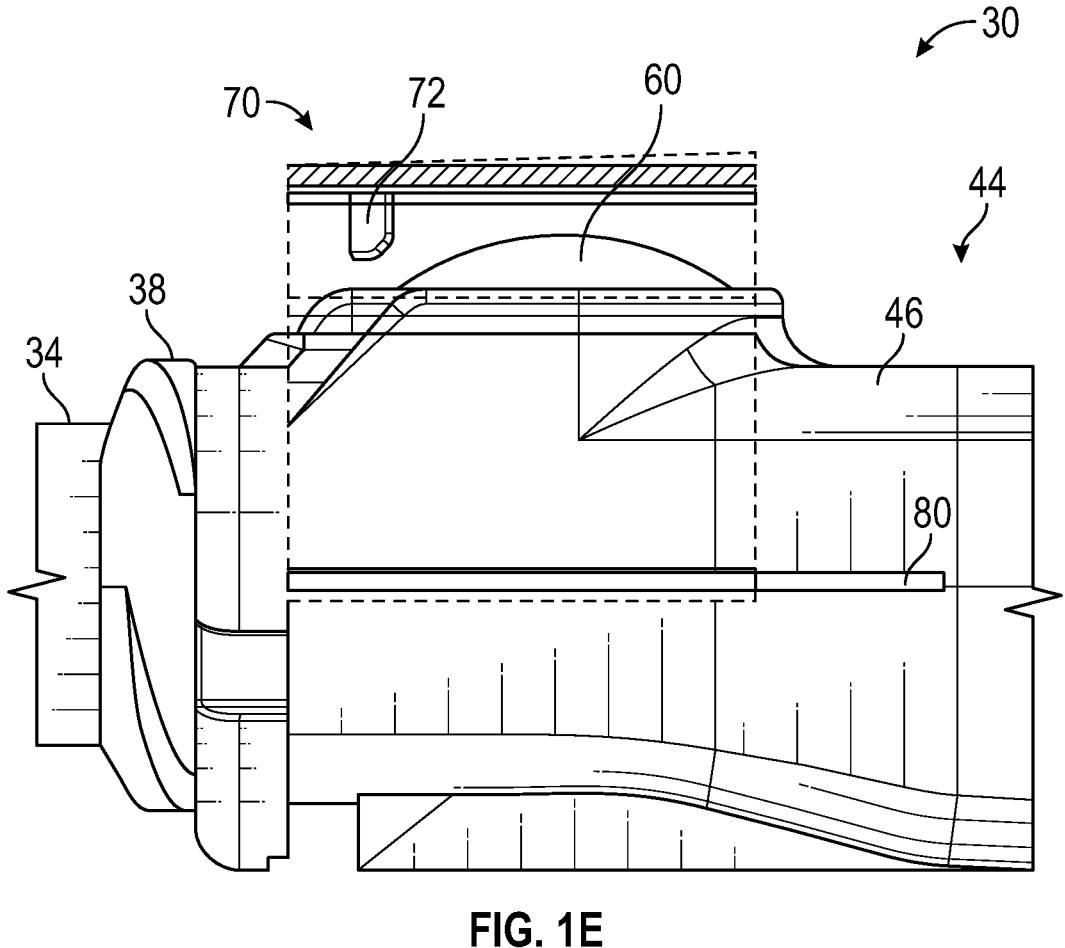
FIG. 1E is a side view of the catheter system of FIG. 1B, according to some embodiments.
Figure 1F:
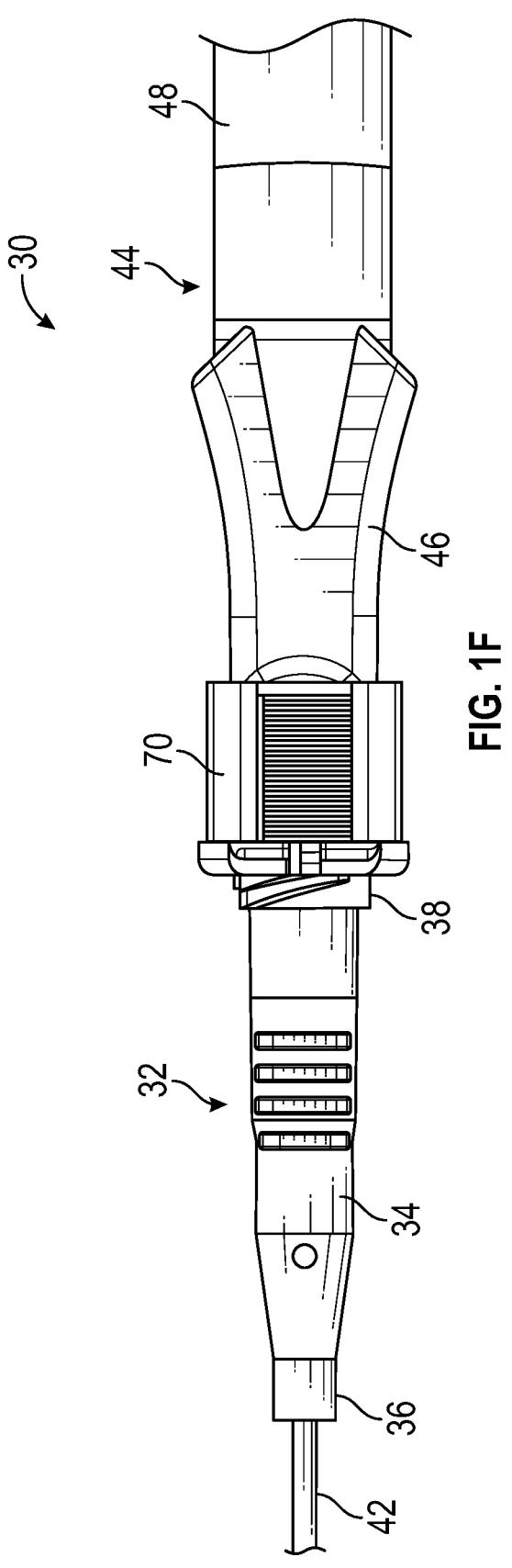
FIG. 1F is a top view of the catheter system of FIG. 1B, according to some embodiments.
Figure 1G:
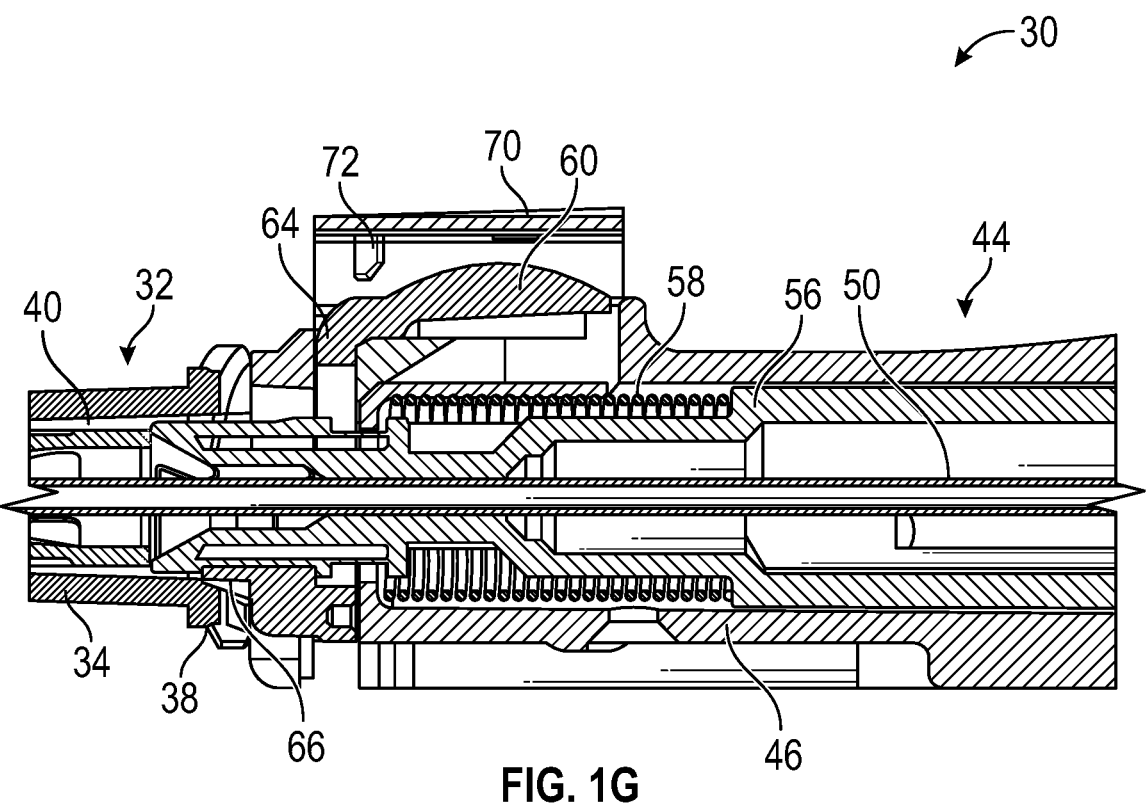
FIG. 1G is a cross-sectional view of the catheter system of FIG. 1B, according to some embodiments.
Figures 1H, 1I:
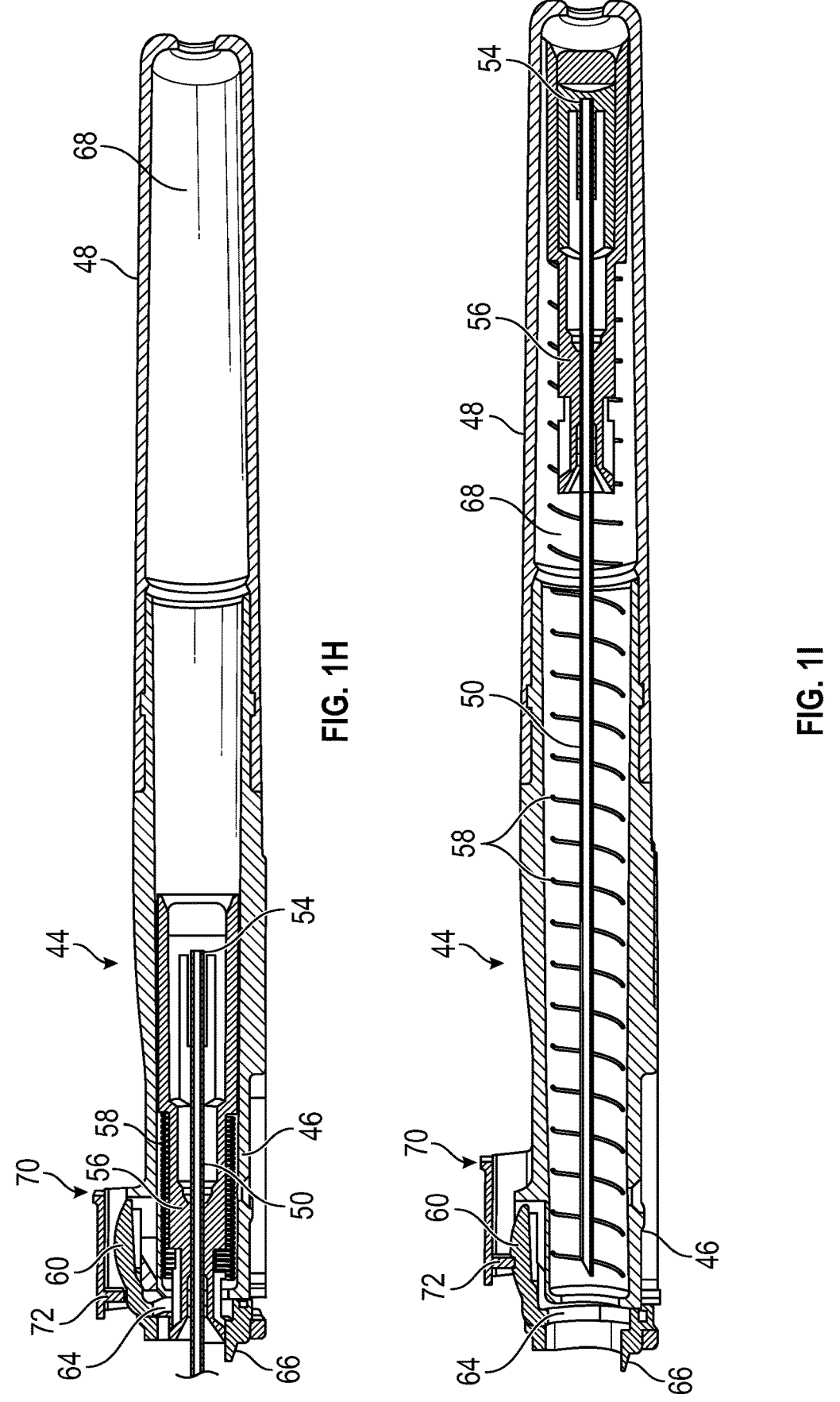
FIG. 1H is a cross-sectional view of the catheter system of FIG. 1B, illustrating an example push-button before depression, according to some embodiments.
FIG. 1I is a cross-sectional view of the catheter system of FIG. 1B, illustrating the push-button after depression, according to some embodiments.
Figure 1J:
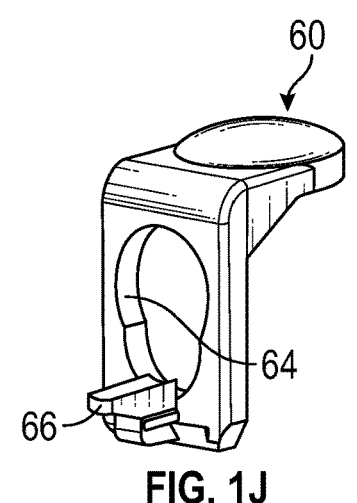
FIG. 1J is an upper perspective view of an example push button, according to some embodiments.
Figure 2A:
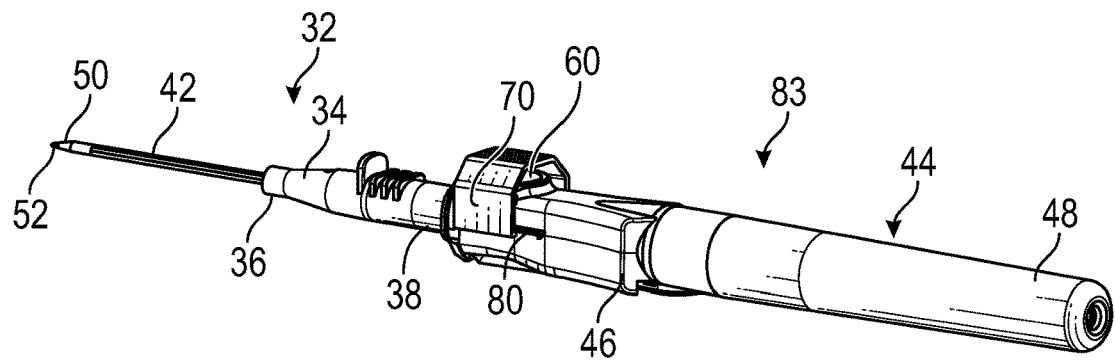
FIG. 2A is an upper perspective view of another catheter system, according to some embodiments.
Figure 2B:
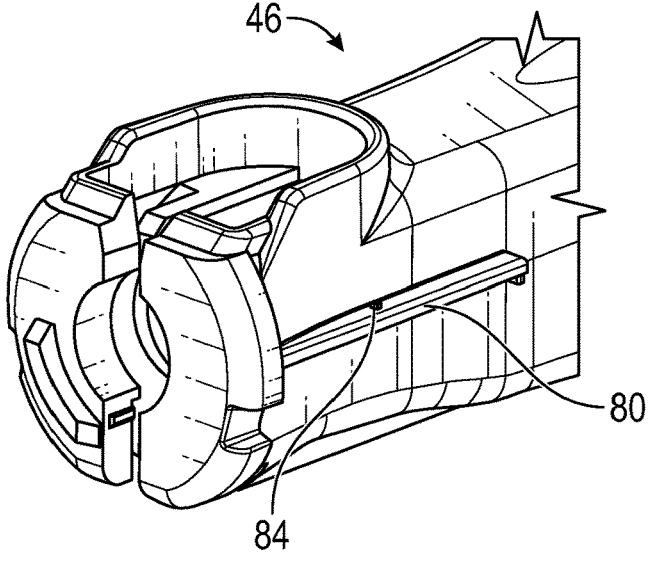
FIG. 2B is an upper perspective view of a distal end of the catheter system of FIG. 2A, according to some embodiments.
Figure 2C:
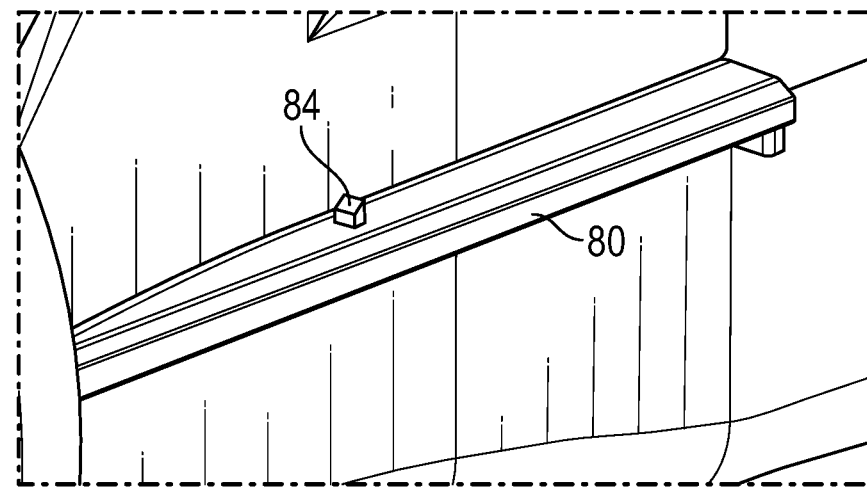
FIG. 2C is an enlarged upper perspective view of an example guide, according to some embodiments.
Figure 2D:
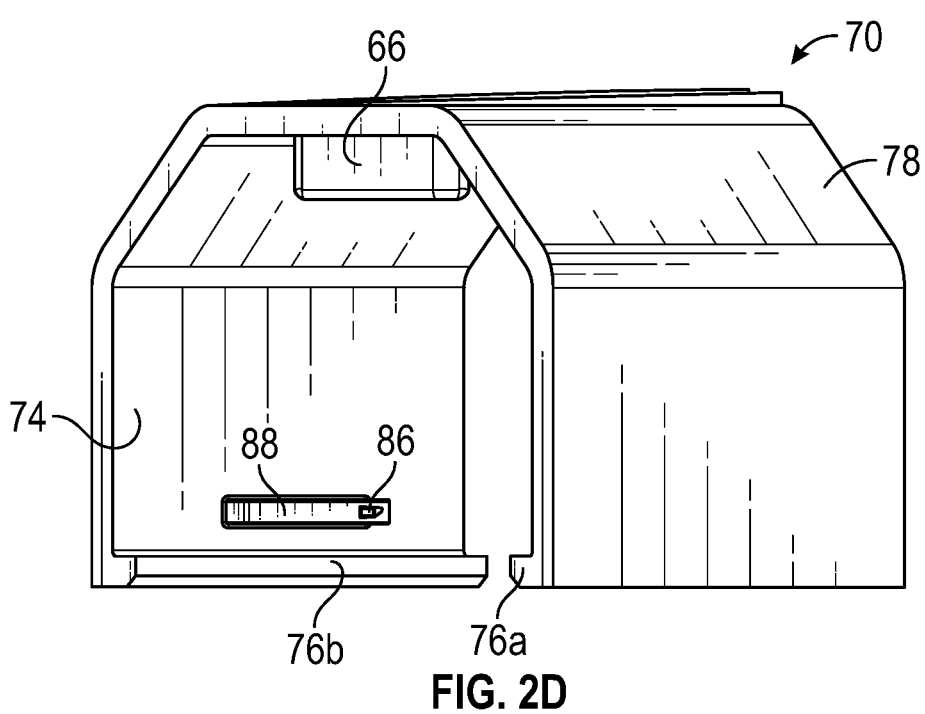
FIG. 2D is a lower perspective view of the cover, according to some embodiments.
Figure 2E:
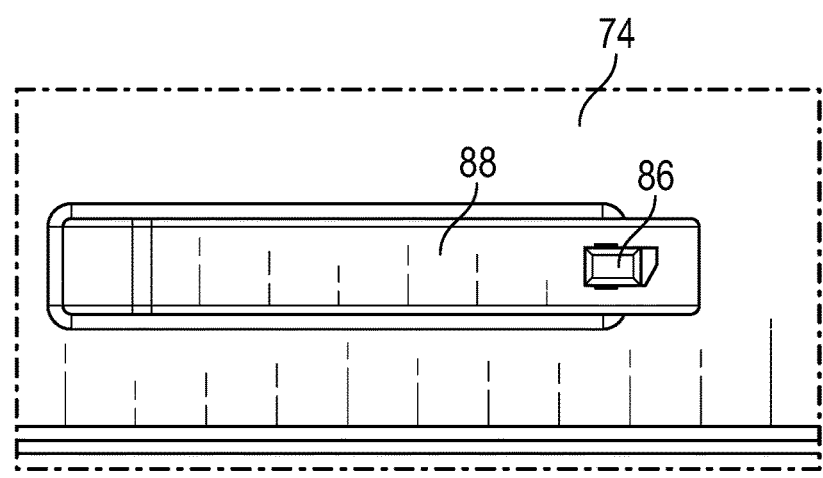
FIG. 2E is an enlarged side view of another example rail, according to some embodiments.
Figure 2F:
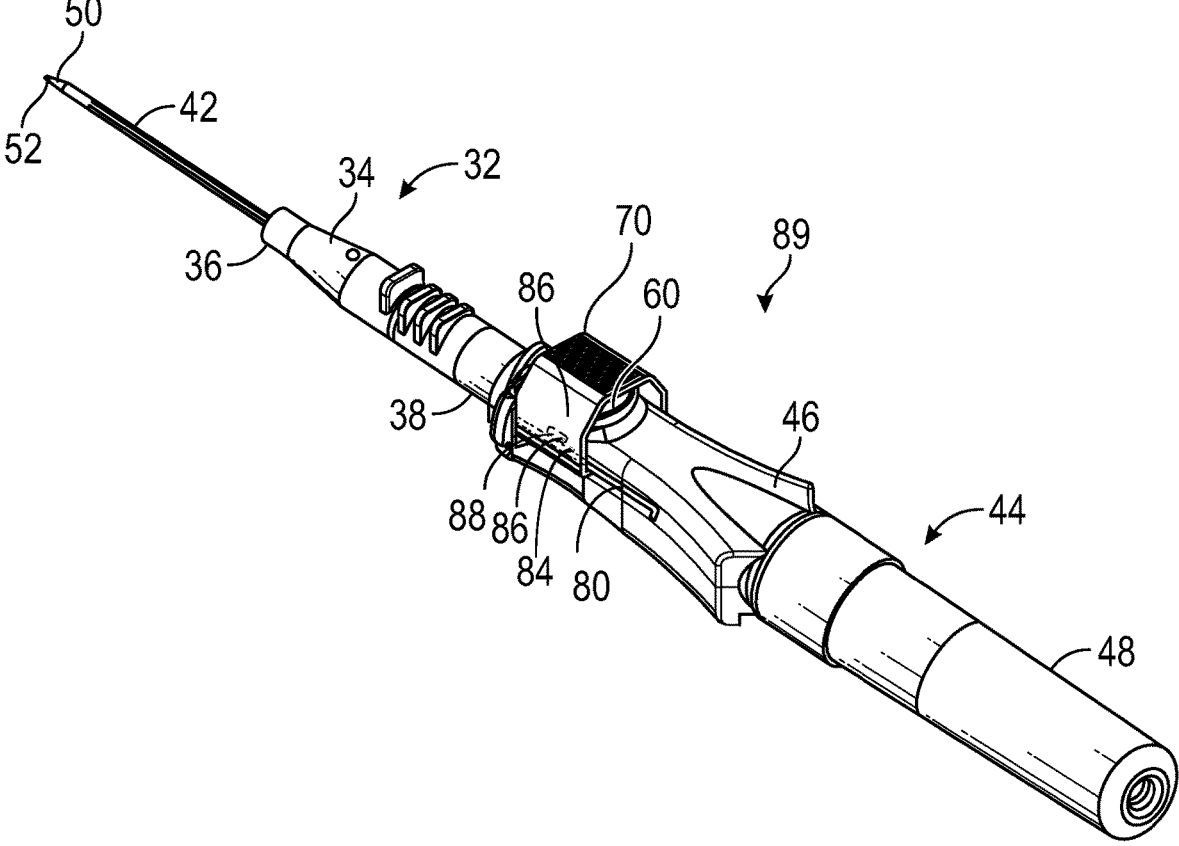
FIG. 2F is an upper perspective view of the catheter system of FIG. 2A, according to some embodiments.
Figure 3A:
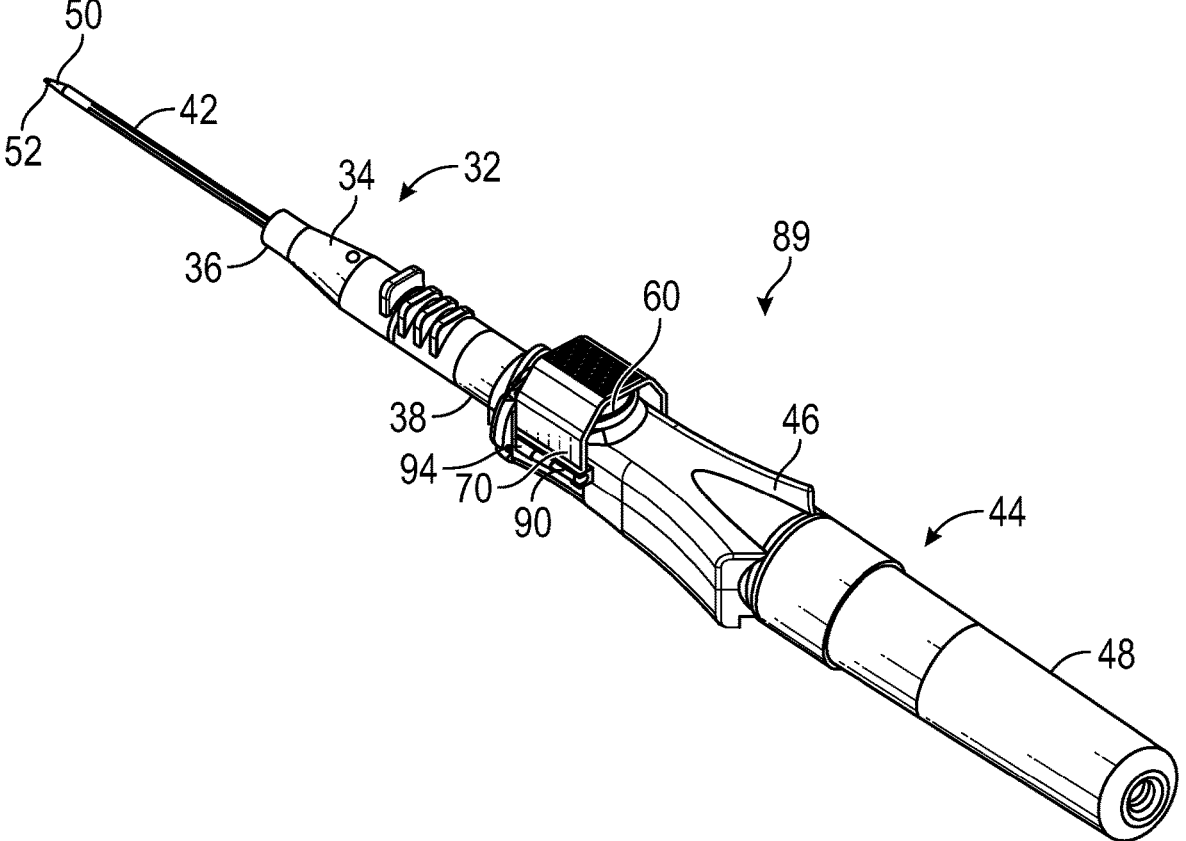
FIG. 3A is an upper perspective view of another example catheter system, according to some embodiments.
Figure 3B:
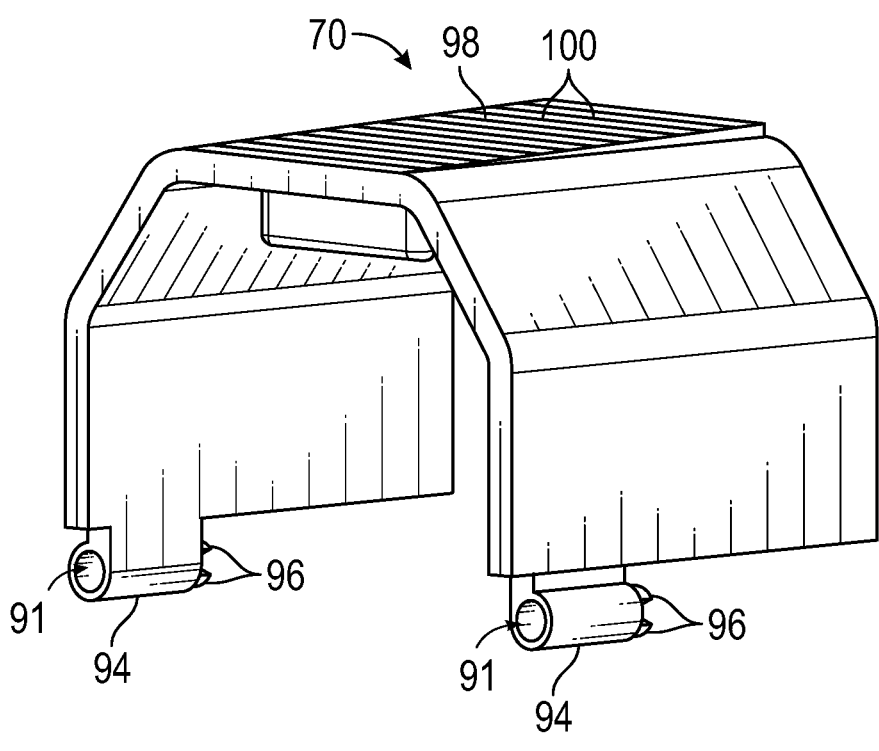
FIG. 3B is an upper perspective view of the cover, according to some embodiments.
Figure 3C:
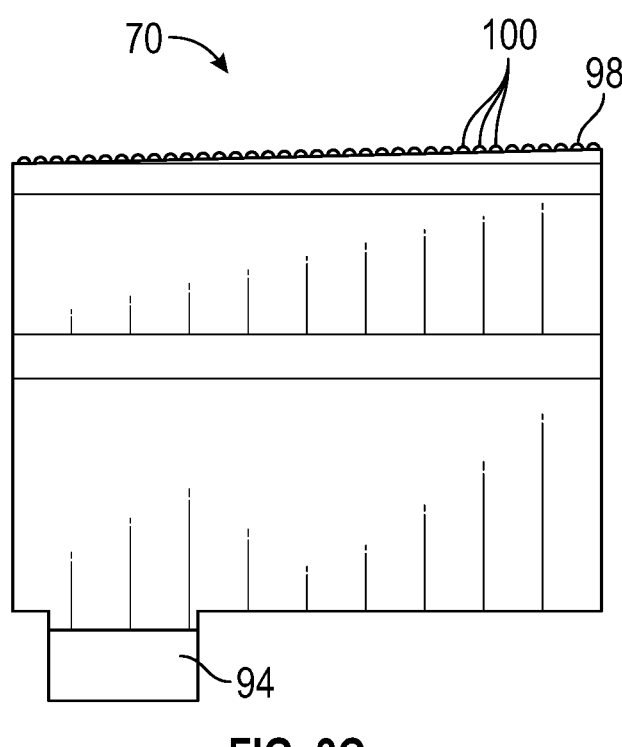
FIG. 3C is a side view of the cover of FIG. 3B, according to some embodiments.
Figures 3D, 3E, 3F:
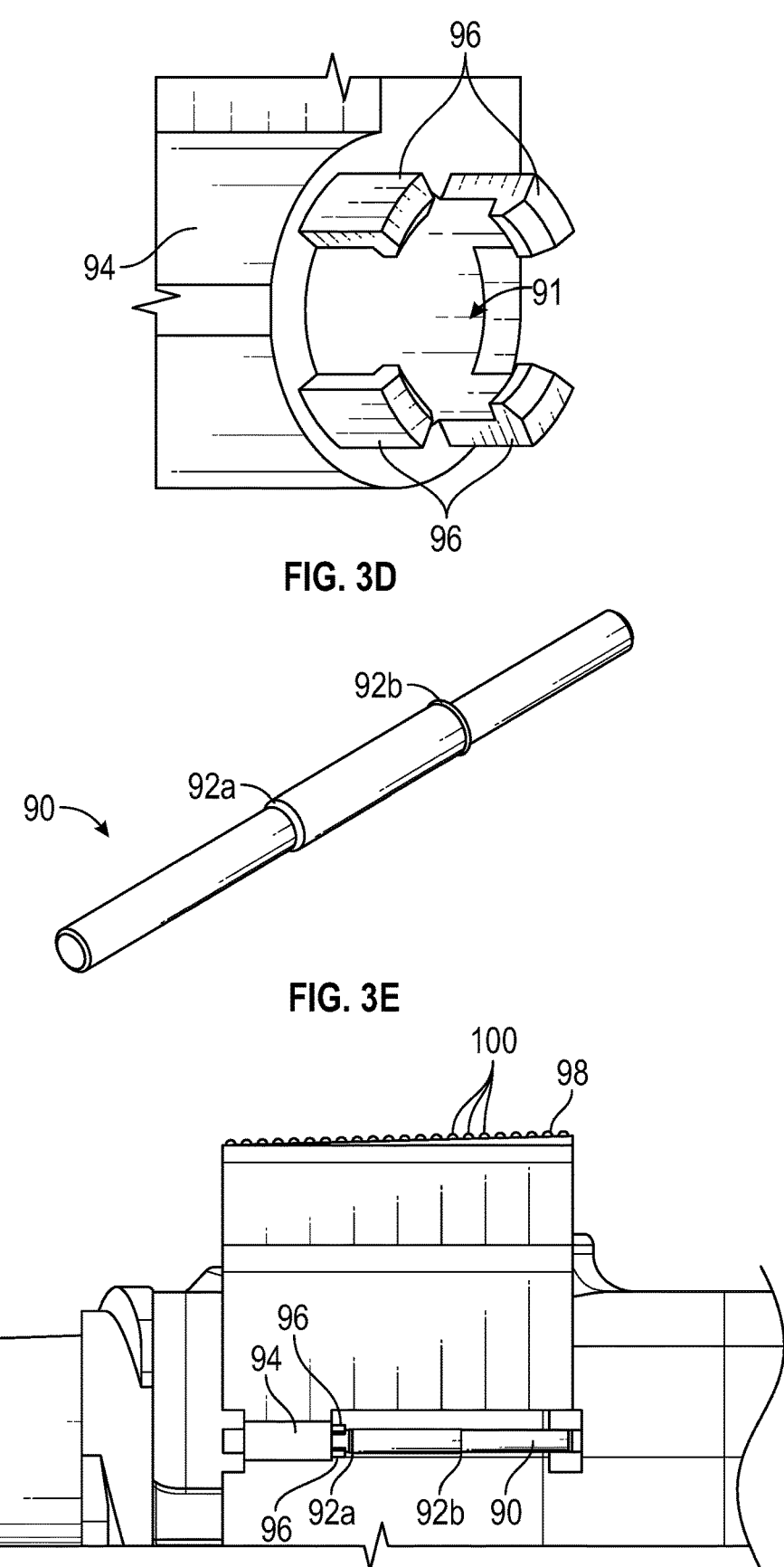
FIG. 3D is a perspective view of example arms, according to some embodiments.
FIG. 3E is an upper perspective view of an example shaft, according to some embodiments.
FIG. 3F is a side view of the catheter system of FIG. 3A, according to some embodiments.
Figure 3G:
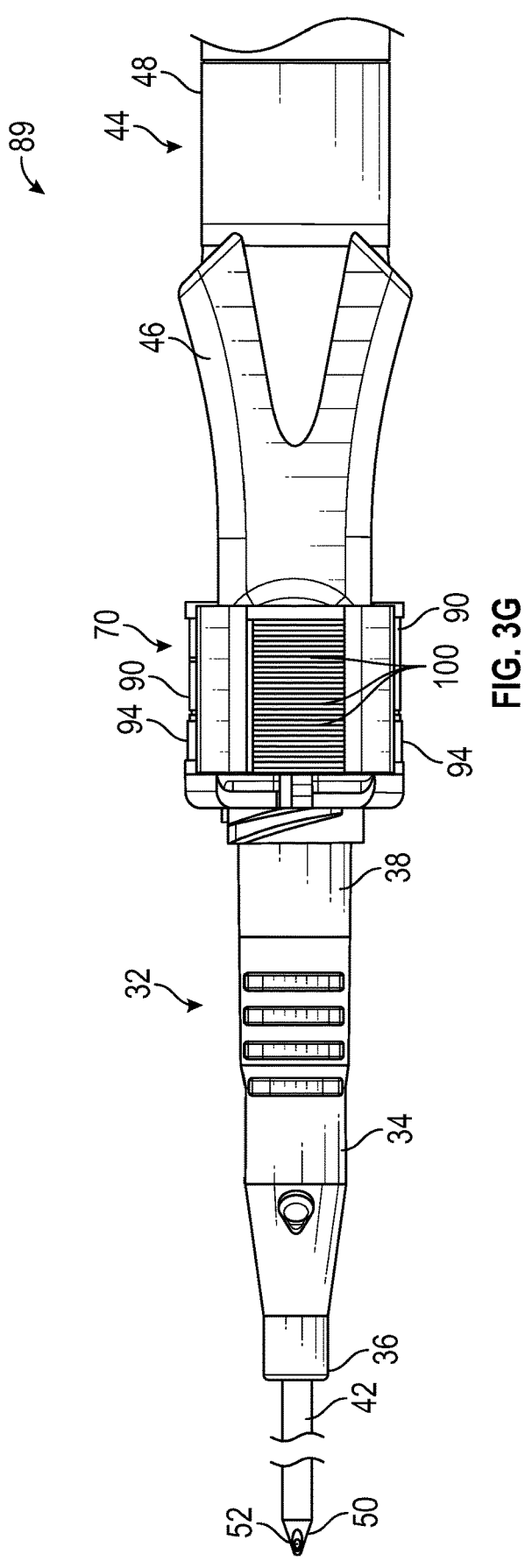
FIG. 3G is a top view of the catheter system of FIG. 3G, according to some embodiments.
Figure 4A:
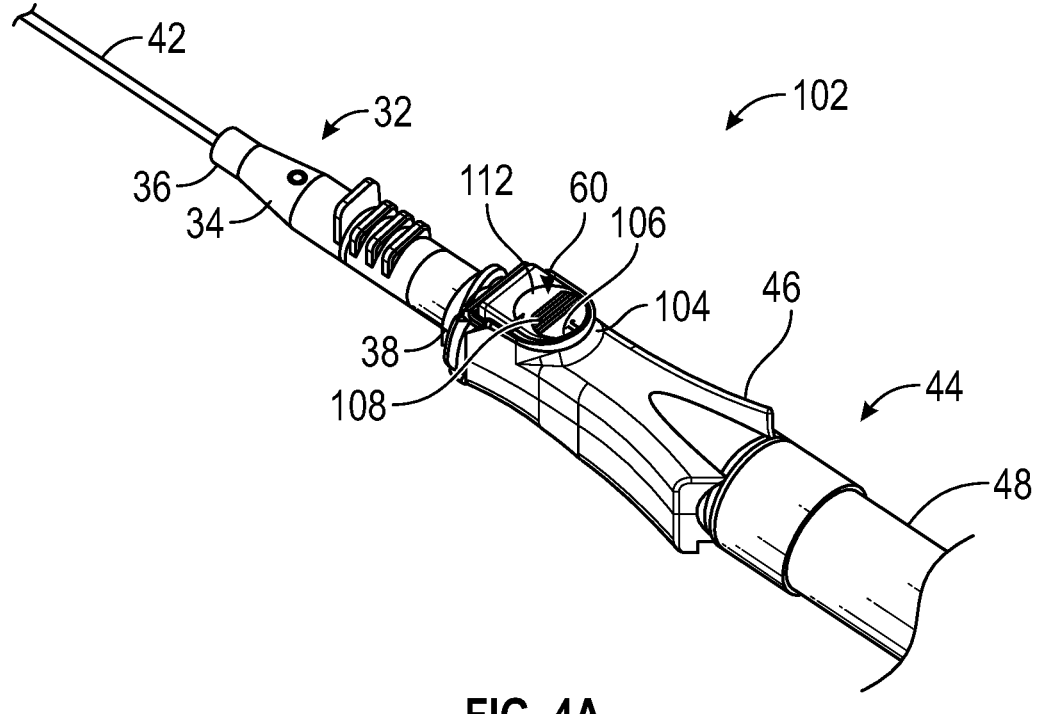
FIG. 4A is an upper perspective view of another catheter system, according to some embodiments.
Figure 4B:
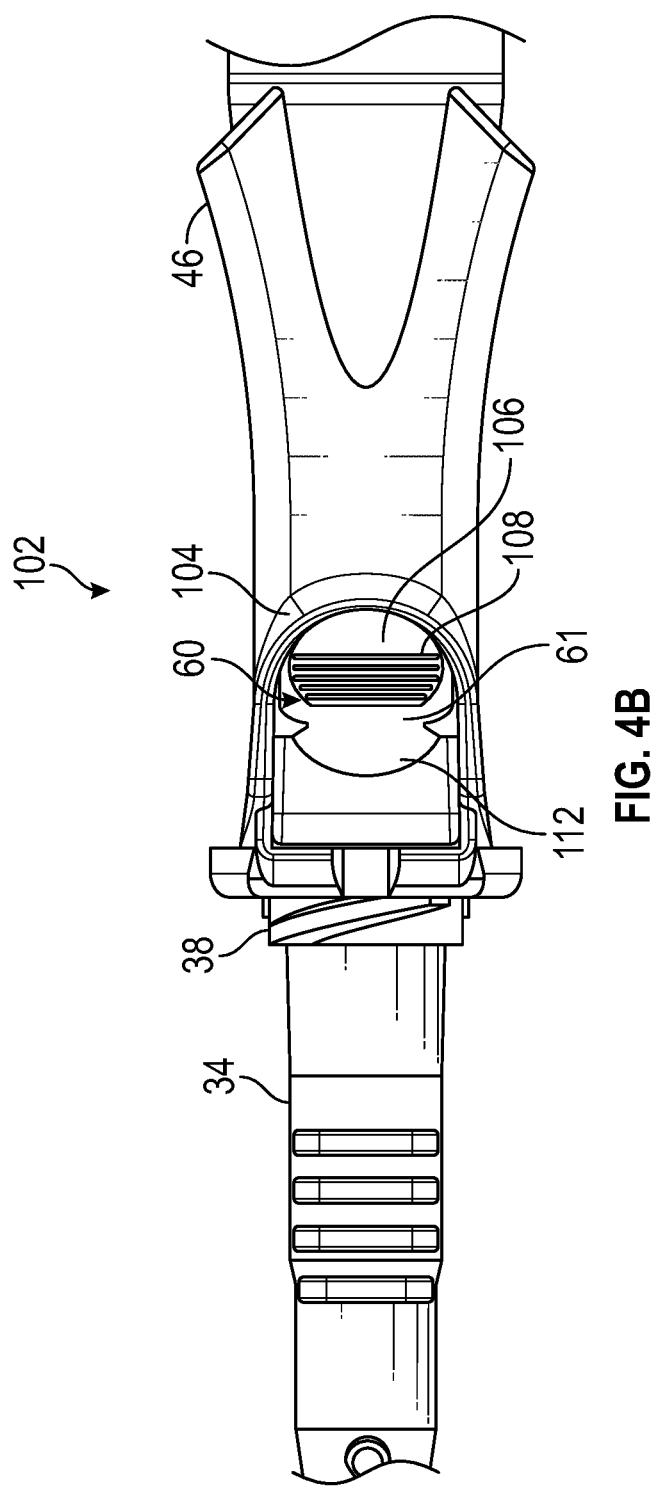
FIG. 4B is a top view of the catheter system of FIG. 4A, according to some embodiments.
Figure 4C:
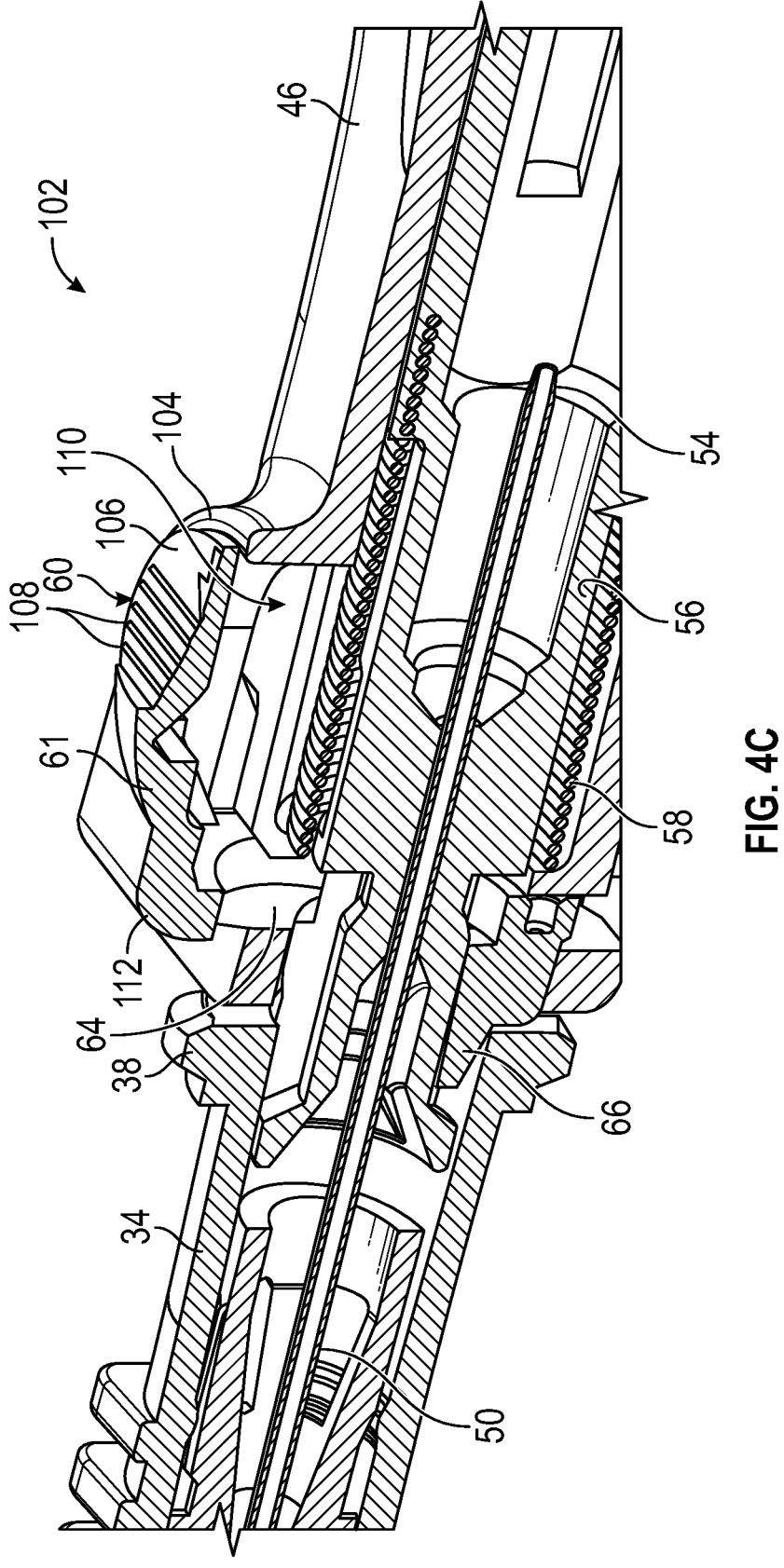
FIG. 4C is a cross-sectional view of the catheter system of FIG. 4A, according to some embodiments.
Figure 4D:
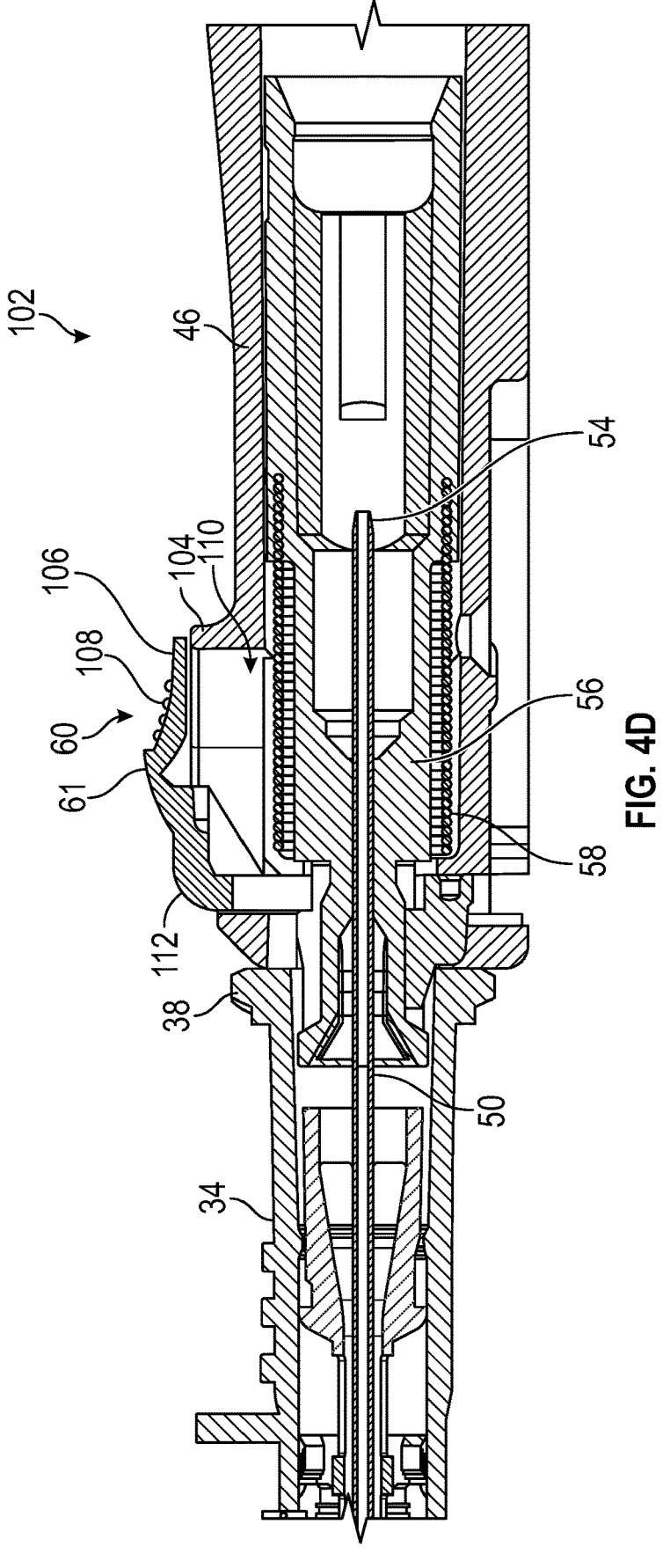
FIG. 4D is another cross-sectional view of the catheter system of FIG. 4A, illustrating an example push button in a proximal position, according to some embodiments.
Figure 4E:
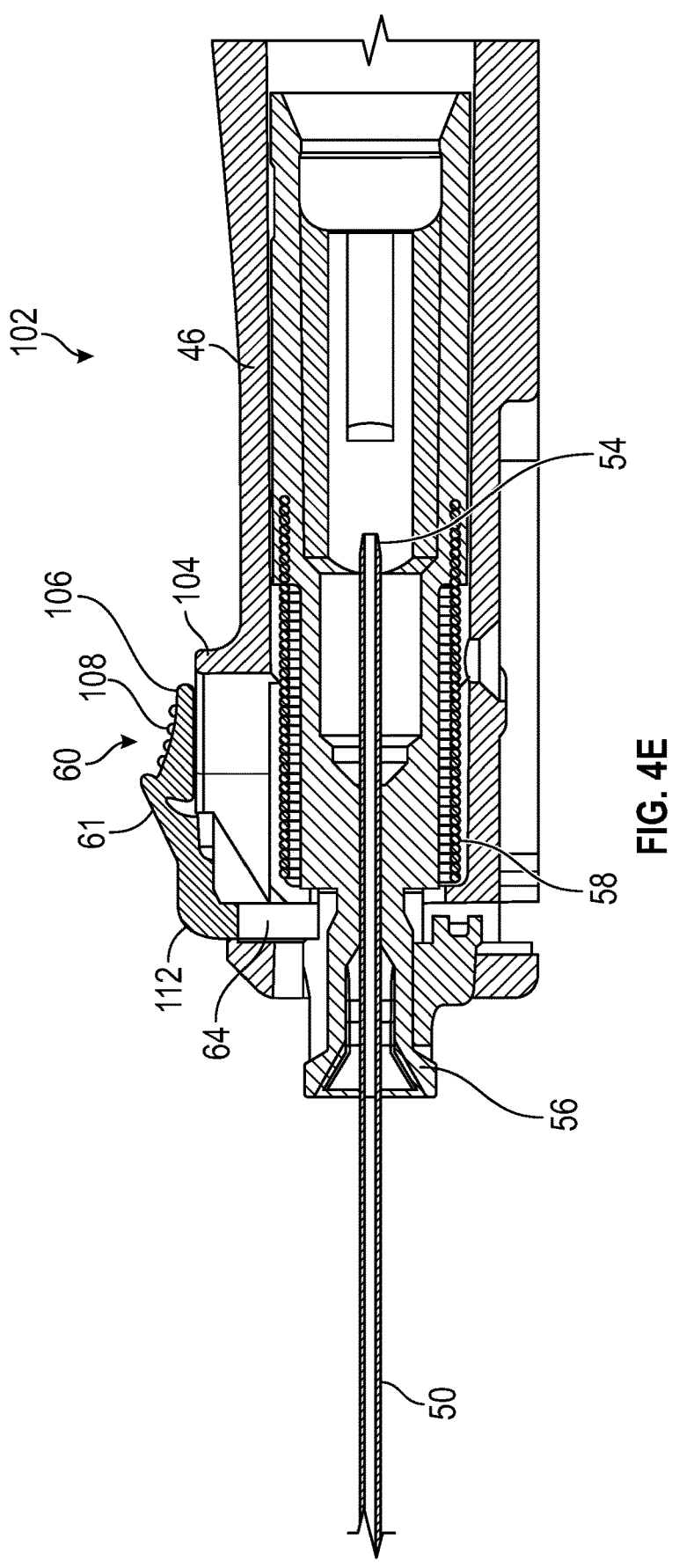
FIG. 4E is another cross-sectional view of the catheter system of FIG. 4A, illustrating an example push button in a distal position, according to some embodiments.
Figure 4F:
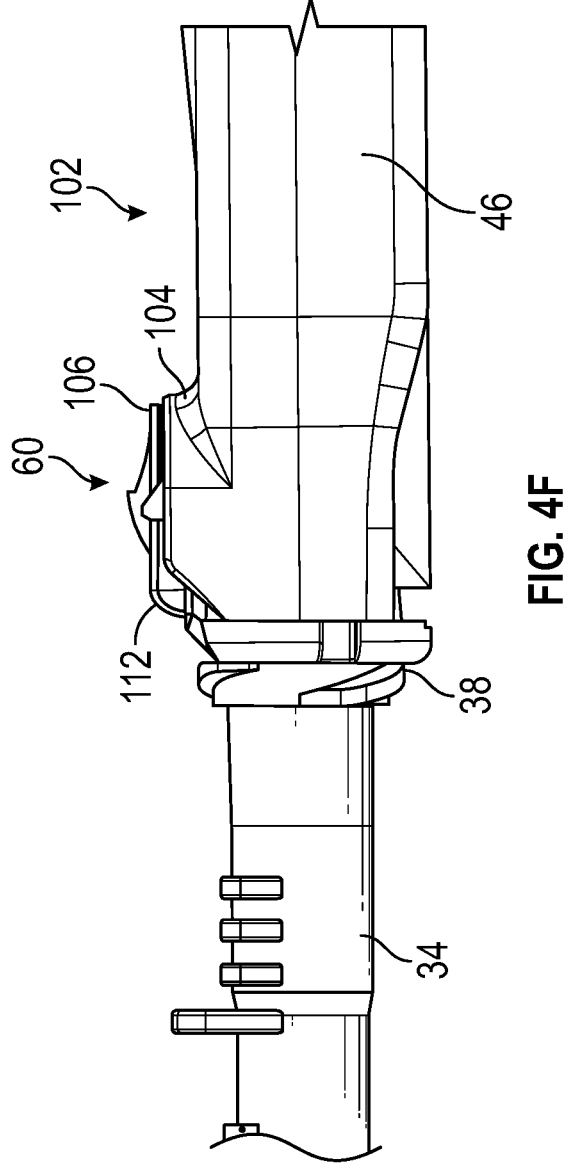
FIG. 4F is a side view of the catheter system of FIG. 4A, according to some embodiments.

As illustrated in FIGS. 1B-1C, in some embodiments, each of the elongated guides 80 may include a groove or slot, which may be generally aligned with the longitudinal axis of the catheter system 30. In some embodiments, the rails 76 may be configured to insert into the elongated guides 80 and slide along the elongated guides 80. In some embodiments, the elongated guides 80 may include a distal end 81 and a proximal end 85.

Referring now to FIGS. 2A-2E, a catheter system 83 is illustrated, according to some embodiments. In some embodiments, the catheter system 83 may be similar or identical to the catheter system 30 of FIGS. 1B-1I in terms of one or more components and/or operation. In some embodiments, each of the elongated guides 80 may include a flange or elongated protrusion, which may be generally aligned with the longitudinal axis of the catheter system 30.

In some embodiments, at least one of the elongated guides 80 may include a housing snap projection 84. In some embodiments, the inner surface 74 of the cover 70 may include a cover snap projection 86. In some embodiments, the housing snap projection 84 may be proximal to the cover snap projection 86. In some embodiments, the cover snap projection 86 may be configured to contact and snap past the housing snap projection 84 in response to the cover 70 sliding proximally, which may facilitate securement of the cover 70 in the first position over top of the push button 60 until intentionally moved by the user.

In some embodiments, the inner surface 74 of the cover 70 may include another rail 88. In some embodiments, the cover snap projection 86 may extend from the other rail 88. In some embodiments, the elongated guide 80 that is the flange or elongated protrusion, may be disposed between the other rail 88 and the rail 76. In some embodiments, the elongated guide 80 may contact the other rail 88 and the rail 76 to facilitate smooth sliding of the cover 70 through a space between the other rail 88 and the rail 76. In some embodiments, the inner surface 74 may include the cover snap projection 86 and another similar cover snap projection opposite the cover snap projection 86. In some embodiments, the other similar cover snap projection may extend from another rail that is similar to and opposite the other rail 88 and spaced apart from the rail 76a (see FIG. 2D, for example), which may contact a particular elongated guide 80.

Referring now to FIGS. 3A-3G, a catheter system 89 is illustrated, according to some embodiments. In some embodiments, the catheter system 89 may be similar or identical to the catheter system 30 of FIGS. 1B-1I and/or the catheter system 83 of FIGS. 2A-2E in terms of one or more components and/or operation. In some embodiments, the needle assembly 44 may include multiple shafts 90, such as a first shaft and a second shaft, disposed on opposing sides of the housing 46. In some embodiments, the shafts 90 may be cylindrical or another suitable shape configured to facilitate sliding of the cover 70 along the shafts 90. In some embodiments, the cover 70 may be configured to slide along the shafts 90. In some embodiments, the cover 70 may include multiple openings 91 on opposing sides of the cover 70. In some embodiments, the shafts 90 may extend through the openings 91.

In some embodiments, each of the shafts 90 may include at least one step 92, which may include an annular ring. In some embodiments, the at least one step 92 may be configured to contact the cover 70 to provide resistance to proximal movement of the cover 70. In some embodiments, the cover 70 may include multiple rings 94 forming the openings 91. In some embodiments, multiple arms 96 may extend proximally from the rings 94. In some embodiments, the at least one step 92 may contact the arms 96 during sliding of the cover 70 proximally to increase friction or resistance between the arms 96 and the shafts 90. In these and other embodiments, the arms 96 may be configured to bias outwardly to pass the at least one step 92 in response to the linear force applied by the user.

In some embodiments, the shafts 90 may include a first step 92a and a second step 92b proximal to the first step 92a, which may provide a dual step snap engagement mechanism. In further detail, in some embodiments, the arms 96 may be configured to snap onto the first step 92a when the cover 70 is in the first position, providing securement of the cover 70 in the first position. In some embodiments, in response to the linear force, the cover 70 may be slid proximally to the second position in which the arms 96 may snap onto the second step 92*b*. In these and other embodiments, the arms 96 may include a protrusion or hook shape to facilitate snapping onto the at least one step 92.

In some embodiments, a top surface 98 of the cover 70 may be angled upwardly in a proximal direction, which may facilitate placement of a digit of the user on the top surface 98 to slide the cover 70 from the first position to the second position. In some embodiments, the top surface 98 may include multiple ribs 100 extending generally perpendicular to the longitudinal axis of the catheter system 30. In some embodiments, the ribs 100 may facilitate gripping by the digit of the user. In some embodiments, the cover 70 may be activated or slid using a single digit or dual digits.

Referring now to FIGS. 4A-4F, a catheter system 102 is illustrated, according to some embodiments. In some embodiments, the catheter system 102 may include or correspond to one or more of the following in terms of one or more components and/or operation: the catheter system 89 of FIGS. 3A-3G, the catheter system 30 of FIGS. 1B-1I, and the catheter system 83 of FIGS. 2A-2E.

In some embodiments, the push button 60 may include a living hinge 61. In some embodiments, the push button 60 may be one piece that is monolithically formed as a single unit. In some embodiments, the housing 46 may include a flange 104 contacting or interfering with a proximal end 106 of the push button 60 to prevent the proximal end 106 of the push button 60 from being depressed. In some embodiments, in response to bending of the living hinge 61 by the user such that the proximal end 106 of the push button 60 is brought closer to a distal end 112 of the push button 60, the proximal end 106 of the push button 60 may be configured to move distal to the flange 104.

In some embodiments, the push button 60 with the proximal end 106 moved distal to the flange may be configured to depress when the catheter adapter 34 is spaced apart from the housing 46 (such that the projection 66 allows depression of the push button 60). In some embodiments, the push button 60 may not include the projection, and the push button 60 moved distal to the flange may be configured to depress when the catheter adapter 34 is spaced apart from the housing 46 is spaced apart from the housing 46 or proximate the housing 46. In some embodiments, in response to depression of the push button 60, the spring 58 may be configured to expand proximally and move the needle hub 56 proximally within the barrel 48 to retract the introducer needle 50 proximally.

In some embodiments, a shape of the push button 60 may allow the user to press the push button 60 forward (distally) and then downward (toward a patient when the catheter system 102 is inserted into the patient). In some embodiments, the shape of the push button 60 may allow the user to press the push button 60 forward and downward at a same time. In some embodiments, the proximal end 106 of the push button 60 proximal to the living hinge 61 may include multiple grip features 108, which may facilitate movement of the push button 60 by the user, such as an index finger of the user. In some embodiments, the grip features 108 may extend generally perpendicular to a longitudinal axis of the catheter system 102.

In some embodiments, the flange 104 may be proximate a cavity 110 in the housing 46. In some embodiments, the push button 60 may be configured to depress into the cavity 110 when the proximal end 106 of the push button 60 is moved distal to the flange 104 and/or the catheter adapter 34 is spaced apart from the housing 46. In some embodiments, the distal end 112 of the push button 60 may be proximate the housing 46 when the flange 104 contacts the proximal end 106 of the push button 60, which may prevent leakage of blood from the housing 46 when the introducer needle 50 is retracted into the housing 46. In these embodiments, the distal end 112 of the push button 60 may contact the housing 46 or be slightly spaced apart from the housing 46.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter system, comprising:
   a catheter assembly, comprising:
     a catheter adapter, comprising a distal end, a proximal end, and a catheter adapter lumen extending through the distal end of the catheter adapter and the proximal end of the catheter adapter; and
     a catheter extending from the distal end of the catheter adapter;
   a needle assembly, comprising:
     a housing comprising a barrel;
     an introducer needle comprising a sharp distal tip;
     a needle hub coupled the introducer needle and movably disposed within the barrel;
     a spring disposed within the housing;
     a push button; and
     a cover disposed over the push button, wherein an inner surface of the cover comprises a projection, wherein the cover is configured to slide proximally, wherein in response to the cover sliding proximally, the projection is configured to contact the push button, wherein in response to the projection contacting the push button, the push button is configured to depress, wherein in response to depression of the push button, the spring is configured to expand proximally and move the needle hub proximally within the barrel to retract the introducer needle proximally.

2. The catheter system of claim 1, wherein the cover is U-shaped and configured to fit over a top of the needle assembly.

3. The catheter system of claim 1, wherein the inner surface of the cover comprises a plurality of rails on opposing sides of the inner surface of the cover, wherein an outer surface of the housing comprises a plurality of elongated guides on opposing sides of the housing and contacting the plurality of rails, wherein the plurality of rails are configured to slide along the plurality of elongated guides when the cover slides proximally.

4. The catheter system of claim 3, wherein each of the plurality of elongated guides comprises a groove.

5. The catheter system of claim 3, wherein each of the plurality of elongated guides comprises a flange.

6. The catheter system of claim 5, wherein at least one of the plurality of elongated guides comprises a housing snap projection, wherein the inner surface of the cover further comprises a cover snap projection, wherein the housing snap projection is proximal to the cover snap projection, wherein the cover snap projection is configured to snap past the housing snap projection in response to the cover sliding proximally.

7. The catheter system of claim 6, wherein the inner surface of the cover comprises another rail, wherein the cover snap projection extends from the other rail.

8. The catheter system of claim 1, wherein the needle assembly further comprises a plurality of shafts disposed on opposing sides of the housing, wherein the cover is configured to slide along the plurality of shafts.

9. The catheter system of claim 8, wherein the cover comprises a plurality of openings on opposing sides of the cover, wherein the plurality of shafts extend through the plurality of openings.

10. The catheter system of claim 9, wherein the cover comprises a plurality of rings forming the plurality of openings, wherein the cover further comprises a plurality of arms extend proximally from the plurality of rings.

11. The catheter system of claim 8, wherein each of the plurality of shafts comprises at least one step.

12. The catheter system of claim 11, wherein the at least one step is configured to contact the cover to provide resistance to proximal movement of the cover.

13. The catheter system of claim 1, wherein a top surface of the cover is angled upwardly in a proximal direction.

14. The catheter system of claim 13, wherein the top surface comprises a plurality of ribs extending generally perpendicular to a longitudinal axis of the catheter system.

15. The catheter system of claim 1, wherein the push button comprises a projection for engagement with the catheter adapter to prevent depression of the push button when the catheter adapter is proximate the housing.

\*   \*   \*   \*   \*